US012714318B2

(12) United States Patent
Sun et al.

(10) Patent No.: US 12,714,318 B2
(45) Date of Patent: Aug. 25, 2026

(54) DEVICE, SYSTEM AND METHOD FOR DETERMINING PULSE PRESSURE VARIATION OF A SUBJECT

(71) Applicant: KONINKLIJKE PHILIPS N.V., Eindhoven (NL)

(72) Inventors: Shaoxiong Sun, Eindhoven (NL); Wouter Herman Peeters, Waalre (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 153 days.

(21) Appl. No.: 17/939,413

(22) Filed: Sep. 7, 2022

(65) Prior Publication Data

US 2023/0000369 A1 Jan. 5, 2023

Related U.S. Application Data

(63) Continuation of application No. 16/470,356, filed as application No. PCT/EP2017/084595 on Dec. 27, 2017, now abandoned.

(30) Foreign Application Priority Data

Jan. 4, 2017 (EP) .................................... 17150242

(51) Int. Cl.
*A61B 5/021* (2006.01)
*A61B 5/00* (2006.01)

(52) U.S. Cl.
CPC ........ *A61B 5/02108* (2013.01); *A61B 5/7225* (2013.01); *A61B 5/725* (2013.01)

(58) Field of Classification Search
CPC ... A61B 5/02108; A61B 5/7225; A61B 5/725; A61B 5/02416
See application file for complete search history.

(56) References Cited

U.S. PATENT DOCUMENTS 8,679,028 B2 3/2014 Melker et al.
11,229,374 B2 1/2022 Al-Ali
(Continued)

FOREIGN PATENT DOCUMENTS

EP 2392256 A1 12/2011
EP 2303104 B1 2/2014
(Continued)

OTHER PUBLICATIONS

Derichard et al., "Automated pulse pressure and stroke vol. variations from radial artery: evaluation during major abdominal surgery", British Journal of Anaesthesia, 103(5), 678-684, 2009.
(Continued)

*Primary Examiner* — Andrey Shostak
(74) *Attorney, Agent, or Firm* — Brynne J. Corcoran

(57) ABSTRACT

The present invention relates to a device, system and method for determining pulse pressure variation of a subject. To enable more reliably determining pulse pressure variation of a subject the device comprises a signal input (11) configured to obtain an input signal representing a hemodynamic signal of the subject, a processor (12) configured to process the input signal and compute a pulse pressure variation and a signal output (13) configured to output the computed pulse pressure variation. The pulse pressure variation is computed by deriving a pulse height signal from the input signal, deriving a pulse height baseline and a de-trended pulse height signal from the pulse height signal as the ratio between the difference between extrema of the de-trended pulse height signal and the respective value of the pulse height baseline signal, and computing the pulse pressure variation from the de-trended pulse height signal and the pulse height baseline.

10 Claims, 7 Drawing Sheets

(56) References Cited

U.S. PATENT DOCUMENTS

| | | | | |
|---|---|---|---|---|
| 2010/0152560 | A1* | 6/2010 | Turcott .................. | A61B 5/415 600/323 |
| 2010/0292584 | A1* | 11/2010 | Lee ........................ | A61B 5/021 600/485 |
| 2011/0077474 | A1 | 3/2011 | Huiku | |
| 2011/0270097 | A1 | 11/2011 | Aboy | |
| 2012/0157860 | A1 | 6/2012 | Suzuki | |
| 2014/0316278 | A1* | 10/2014 | Addison .............. | A61B 5/7278 600/476 |
| 2014/0316287 | A1 | 10/2014 | Watson et al. | |
| 2014/0323822 | A1 | 10/2014 | Addison et al. | |
| 2014/0323876 | A1* | 10/2014 | McGonigle ........ | A61B 5/02433 600/476 |
| 2015/0190096 | A1* | 7/2015 | Zong .................. | A61B 5/14532 600/301 |
| 2016/0038041 | A1 | 2/2016 | Clinton | |
| 2016/0038097 | A1 | 2/2016 | Jian et al. | |
| 2020/0100686 | A1 | 4/2020 | Sun | |

FOREIGN PATENT DOCUMENTS

| | | |
|---|---|---|
| JP | 2015080624 A | 4/2015 |
| WO | 2015049113 A1 | 4/2015 |
| WO | 2016097935 A1 | 6/2016 |

OTHER PUBLICATIONS

International Search Report and Written Opinion, International Application No. PCT/EP2017/084595, Mailed on Apr. 12, 2018.

Aboy, M. et al., "A Novel Algorithm to Estimate the Pulse Pressure Variation Index", IEEE Transactions on Biomedical Engineering, vol. 51, No. 12, Dec. 2004.

Aboy, M. et al., "An Enhanced Automatic Algorithm for Estimation of Respiratory Variations in Arterial Pulse Pressure During Regions of Abrupt Hemodynamic Changes", IEEE Transactions on Biomedical Engineering, vol. 56, No. 10, Oct. 2009.

Addison, P. et al., "On Better Estimating and Normalizing the Relationship between Clinical Parameters: Comparing Respiratory Modulations in the Photoplethysmogram and Blood Pressure Signal (DPOP versus PPV)", Hindawi Publishing Corporation, Computational and Mathematical Methods in Medicine, 2014.

Cannesson, M. et al., "Respiratory Variations in Pulse Oximetry Plethysmographic Waveform Amplitude to Predict Fluid Responsiveness in the Operating Room", Anesthesiology 2007; 106:1105-11.

Cannesson, M. et al., "Does the Pleth Variability Index Indicate the Respiratory-Induced Variation in the Plethysmogram and Arterial Pressure Waveforms?", vol. 106, No. 4, Apr. 2008.

Cannesson, M. et al., "Pulse Pressure Variation: Where Are We Today?", Journal of Clinical Monitoring and Computing, 2010.

Derichard, A. et al., "Automated pulse pressure and stroke volume variations from radial artery: evaluation during major abdominal surgery", British Journal of Anaesthesia 103 (5): 678-84 (2009).

Diepen, S., "Modeling respiratory induced variations in blood pressure", Eindhoven University of Technology, Department of Electrical Engineering, 2006.

Michard, F. et al., "Relation between Respiratory Changes in Arterial Pulse Pressure and Fluid Responsiveness in Septic Patients with Acute Circulatory Failure", Am J Respir Crit Care Med vol. 162. pp. 134-138, 2000.

Addison, P. et al., "Increasing signal processing sophistication in the calculation of the respiratory modulation of the photoplethysmogram (DPOP)", J Clin Monit Comput (2015) 29:363-372.

* cited by examiner

DEVICE, SYSTEM AND METHOD FOR DETERMINING PULSE PRESSURE VARIATION OF A SUBJECT

CROSS REFERENCE TO RELATED APPLICATION

The present application is a continuation of co-pending U.S. patent application Ser. No. 16/470,356, filed Jun. 17, 2019, which is the U.S. National Phase application under 35 U.S.C. § 371 of International Application No. PCT/EP2017/084595 filed Dec. 27, 2019, which claims the benefit of European Application No. EP17150242.0 filed Jan. 4, 2017. These applications are hereby incorporated by reference herein.

FIELD OF THE INVENTION

The present invention relates to a device, system and method for determining pulse pressure variation of a subject.

BACKGROUND OF THE INVENTION

Optimal circulatory volume status is important for patients in the operating room (OR) and the intensive care unit (ICU). On the one hand, hypovolemia can lead to inadequate oxygen delivery to tissues. On the other hand, hypervolemia can induce tissue edema and oxygen delivery alteration. Hemodynamic optimization, in the aim of optimal circulatory volume, has been shown to be able to improve postoperative outcome and reduce the cost of the surgery.

Unfortunately, circulatory volume status cannot be assessed directly. Fluid responsiveness has been used as an indirect assessment of volume status. It answers the question if a patient's cardiac output and hence hemodynamics can be increased by giving fluid. If not, extra fluid loading may cause complications. To evaluate fluid responsiveness, static indicators and dynamic indicators have been proposed.

Static indicators such as central venous pressure (CVP), or left ventricular end-diastolic area have been demonstrated to have poor performance for assessing fluid responsiveness.

Dynamic indicators, relying on the cardiopulmonary interactions, have been shown to be better predictors for patients undergoing mechanical ventilation. The rationale is that mechanical ventilation induces cyclic changes in the intrathoracic pressure (i.e., the external pressure on the heart muscle). The cyclic changes in the intrathoracic pressure can induce cyclic changes in the preload of the heart (the end-diastolic blood volume inside the heart). The cyclic changes in the preload can induce cyclic changes in the stroke volume of the heart, which will appear as cyclic changes in the pulse height of a hemodynamic waveform like the blood pressure waveform or a photoplethysmographic waveform. If the cyclic changes in the intrathoracic pressure result in sufficiently strong cyclic changes of the stroke volume, the patient is predicted to be fluid responsive. If the cyclic changes in the intrathoracic pressure do not result in sufficiently strong cyclic changes of the stroke volume, the patient is predicted not to be fluid responsive.

Pulse pressure variations (PPV; also known as pulse height variations) are designed to quantify the cyclic changes in the pulse height of a hemodynamic waveform. PPV is originally defined on the arterial blood pressure signal and later extended to the photoplethysmographic signal. $PPV (\%)=100\times\{(PH_{max}-PH_{min})/([PH_{max}+PH_{min}]/2)\}$, where PH refers to the pulse height of cardiac pulse in the arterial blood pressure signal or photoplethysmographic signal. During positive pressure ventilation, pulse height increases with inspiration and decreases with expiration. PPV has been shown to be useful for mechanically ventilated patients with acute circulatory failures related to sepsis, and for patients who have undergone coronary artery bypass grafting. In general, the application of PPV has been proven to decrease the length of stay in hospital.

Various PPV algorithms for an ABP (arterial blood pressure) wave can be found in scientific literature. The most straightforward implementation of an algorithm is the literal implementation of the original definition. Some improvements have been made by implementing new methods to derive the pulse-pressure curve, and new methods for post-processing the initial PPV values. Derichard et al., Automated pulse pressure and stroke volume variations from radial artery: evaluation during major abdominal surgery, British Journal of Anaesthesia, 103(5), 678-684, describes an algorithm which has a fixed window length, and has strong post-processing of the initial PPV values.

Known algorithms have various disadvantages. During episodes of hemodynamic changes (e.g. injection of vasoactive medication, injection of inotrope medication, rapid blood loss, application/removal of a blood vessel clamp during surgery, pain stimulus) the computed PPV values are often falsely elevated such that they do not resemble the fluid responsiveness. Further, irregular heartbeats (e.g. premature ventricular contraction or arrhythmia) greatly affect the computed PPV values. Still further, even during situations of stable heart rhythms and no hemodynamic changes, the computation of the PPV value is intrinsically noisy.

Falsely elevated or diminished PPV values are misleading to clinicians and may lead to wrong decisions on fluid loading, resulting in patients with hypovolemia or hypervolemia. These conditions can lead to serious complications.

US 2014/323876 A1 discloses methods and systems for determining fluid responsiveness based on physiological signals. The system may detect gain changes or excessive baseline modulations. In some embodiments, based on the detected gain changes or excessive baseline modulations, the system may ignore portions of physiological signals and determine a parameter indicative of fluid responsiveness based on a plurality of amplitudes determined from other portions of the physiological signals. In some embodiments, based on the detected gain changes or excessive baseline modulations, the system may determine fluid responsiveness, or refrain from determining fluid responsiveness.

SUMMARY OF THE INVENTION

It is an object of the present invention to provide a device, system and method for more reliably determining pulse pressure variation of a subject.

In a first aspect of the present invention a device for determining pulse pressure variation of a subject is presented comprising:

- a signal input configured to obtain an input signal representing a hemodynamic signal of the subject;
- a processor configured to process the input signal and compute a pulse pressure variation by
  - deriving a pulse height signal from the input signal,
  - deriving a pulse height baseline and a de-trended pulse height signal from the pulse height signal,
  - computing the pulse pressure variation from the de-trended pulse height signal and the pulse height baseline as the ratio between the difference between extrema of the de-trended pulse height signal and the respective value of the pulse height baseline signal; and a signal output configured to output the computed pulse pressure variation.

In a further aspect of the present invention a system for determining pulse pressure variation of a subject is presented comprising:

a signal acquisition unit configured to acquire an input signal representing a hemodynamic signal of the subject;

a device as disclosed herein for determining pulse pressure variation of a subject based on the acquired input signal; and a signal issuing unit configured to issue the computed pulse pressure variation.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to solve or else at least alleviate the problems of the known algorithms by introducing a post-processing step after the derivation of the PH signal, and before the computation of the initial PPV-values. Disadvantages of the known algorithms are thus at least partially overcome.

Determining PPV is important to prevent patients in the operating room or the ICU from hypovolemia and hypervolemia. The underlying problem for the PPV computation is that consistent changes in the pulse height, varying phase between cardiac and ventilation cycle, and irregular beats will complicate the PPV computation, generate unreliable values and potentially mislead clinicians. According to the present invention, the baseline is extracted from the PH signal and used as the mean PH signal to compute PPV to suppress the influence of baseline changes and thus avoid generating falsely elevated or diminished PPV values. The present invention thus offers clinical decision support in determining volume status in dynamic scenarios and potential benefits of preventing over-treatment.

According to a preferred embodiment the de-trended pulse height signal is derived by subtracting the pulse height baseline from the pulse height signal. This provides a computationally inexpensive way of obtaining a useful de-trended pulse height signal.

There are different options to obtain information concerning the ventilation frequency of the subject. One option is that the signal input is configured to obtain the ventilation frequency of the subject. Another option is that the processor is configured to determine the ventilation frequency of the subject by extracting an input signal baseline from the input signal and estimating the ventilation frequency from the input signal baseline, in particular from an arterial blood pressure baseline. Still another option is that the processor is configured to determine the ventilation frequency of the subject by extracting the ventilation frequency from the de-trended pulse height signal. The various options require different computation power and may be chosen according to circumstances, e.g. whether or not a sensor for acquiring the ventilation frequency is available.

The present invention may use the finding that a blood pressure baseline is less affected by artefacts than the baseline from a photoplethysmographic (PPG) signal. The dominant frequency in the PPG baseline often differs from the ventilation frequency due to peripheral vasoactive oscillations. In contrast, the blood pressure baseline is less affected by peripheral vasoactive oscillations as the blood pressure is determined by the central blood pressure in the thorax.

In another embodiment the processor is configured to filter the de-trended pulse height signal using a band pass filter around the ventilation frequency of the subject, in particular a band pass filter having an adaptive or predetermined center frequency and/or bandwidth, preferably a center frequency and/or bandwidth set based on the ventilation frequency. The band pass filter may e.g. be a peak filter. With this embodiment the subsequent processing focusses exclusively on the ventilation-induced components to suppress the influence of varying phase between cardiac and ventilation cycle and irregular beats.

The signal input may further be configured to obtain as input signal a signal selected from the group of signals comprising an arterial blood pressure signal, a photoplethysmographic signal, a blood flow signal, a Doppler ultrasound signal, a laser Doppler signal, a speckle-contrast signal, a ballistocardiographic signal, an accelerometer signal, a radio-frequency inductance signal or a bio-impedance signal acquired from the subject.

The processor may preferably be configured to compute the pulse pressure variation from the de-trended pulse height signal or the filtered de-trended pulse height signal in a computing window having a predetermined window length or a window length determined from the ventilation frequency of the subject, in particular having a window length of at least one ventilation cycle or an integer multiple of one ventilation cycle. Hence, the determined ventilation (=respiration frequency), e.g. determined from the baseline of the hemodynamic signal, may be used to set the adaptive window length of the computation of the initial PPV values.

In another embodiment the processor is configured to compute the pulse pressure variation value in a computing window by computing the difference between the maximum value and the minimum value or between an upper threshold value and a lower threshold value of the de-trended pulse height signal in the computing window, said upper threshold value being in a range of 75-99% and the lower threshold value being in a range of 1-25%. This further improves the accuracy of the computation.

The pulse pressure variation is computed as the ratio between the difference between extrema of the de-trended pulse height signal and the respective value (e.g. mean or median) of the pulse height baseline signal.

The processor may further be configured to compute the pulse pressure variation by dividing the computed pulse pressure variation values by the respective values of the pulse height baseline.

Further, in an embodiment the processor may be configured to derive the pulse height signal from the input signal by interpolation, in particular spline interpolation, and low-pass filtering.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
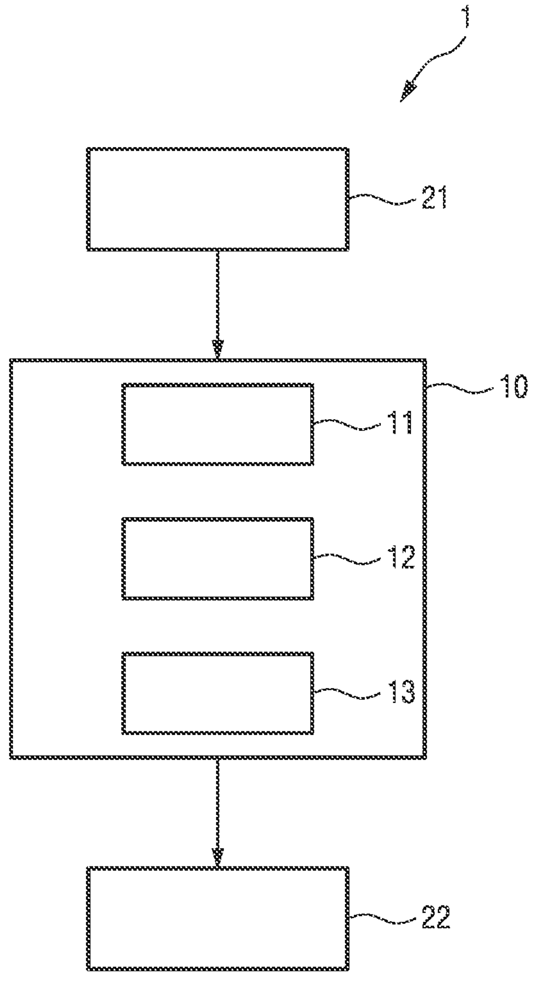
FIG. 1 shows a schematic diagram of an embodiment of a system and a device for determining pulse pressure variation of a subject according to the present invention.

Before details of the present invention shall be explained with reference to the figures, some general thoughts related to the present invention shall be discussed.

The way known algorithms try to alleviate the earlier mentioned problems include the steps of: derivation of the pulse height (PH) signal, computation of initial PPV values, and post processing of the initial PPV values. The known algorithms alleviate the problems by applying considerable post-processing on the computed PPV values, which induces new problems and disadvantages. Post-processing involves averaging over long time-windows, which increases the latency of the algorithms, which is highly unwanted. Furthermore, post-processing of the initially-computed PPV values is often not adequate, and false high values will still be produced.

The technical root causes of the problems and disadvantages are:

i) During episodes of hemodynamic changes, the baseline of the PH signal can rapidly grow or decline. These changes are captured by the known algorithms and will result in elevated PPV values. However, these rapid increases or decreases of the PH signal are not preload-induced (not related to positive pressure ventilation), so these variations do not represent fluid responsiveness.

ii) Irregular heartbeats will generate wildly varying pulse heights. The variations do not relate to fluid responsiveness. This noisy signal will cause the initially computed PPV value to be falsely elevated.

iii) Even during situations of stable heart rhythms and no hemodynamic changes, the known algorithms compute noisy pulse heights, because the exact phase between the heart cycle and the ventilation cycle determines the computed pulse heights. Since this phase varies quickly over time, the computed pulse heights will also vary over time. These variations do not relate to fluid responsiveness either.

These problems and disadvantages can be avoided or else at least alleviated in the following ways by embodiments of device, system and method according to the present invention:

a) According to the present invention the baseline of the pulse height signal is extracted. Because of the extraction of the baseline signal, changes (but still slower than the ventilation rate, i.e., $<0.1$ Hz) in the PH signal are not present anymore and will therefore not disturb the computed initial PPV values. The information of the baseline of the PH signal needs to be reused separately in the computation of the PPV value, which means that this step should not be regarded as removing the baseline, but as extracting the baseline for later use.

b) According to an embodiment of the present invention a band pass filter, in particular an adaptive band pass filter, e.g. a peak (narrow band pass) filter, is applied on the PH signal before the signal will be used for computing the initial PPV values. In this way, any irregularities that occur at a different frequency than the ventilation frequency (like for example an irregular beat that causes an outlier in the PH signal) will be removed from the PH signal.

c) The disadvantage iii) is also solved by applying the adaptive band pass filter provided in an embodiment.

Since this post-processing of the PH signal is applied, there is no need to apply post-processing of the PPV values, which makes the presented algorithm also faster in response to changes of the fluid responsiveness.

Figure 2:
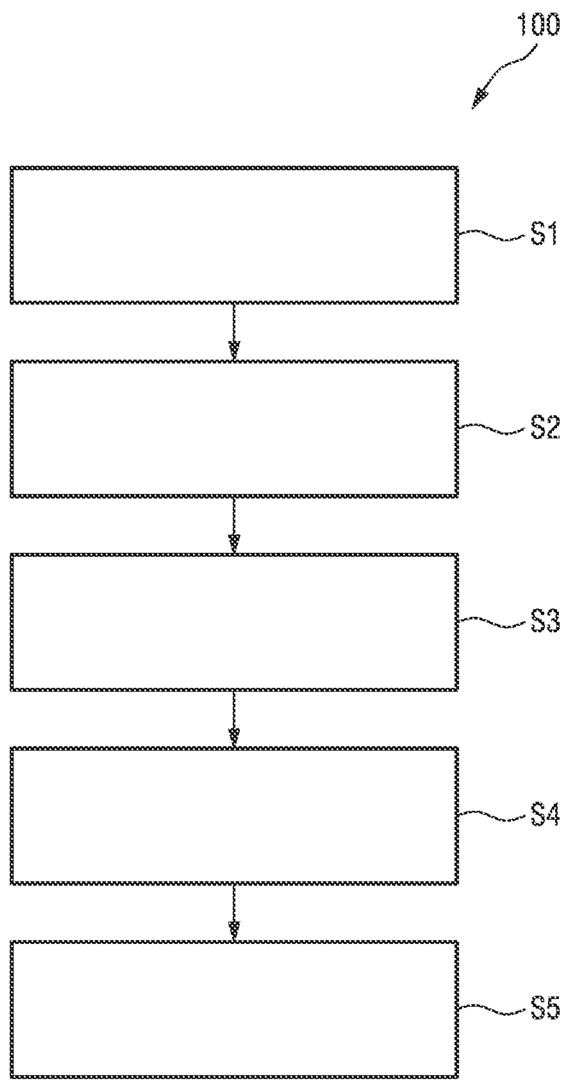
FIG. 2 shows a flow chart of a first embodiment of a method for determining pulse pressure variation of a subject according to the present invention.

Referring now to the drawings, FIG. 1 shows a schematic diagram of an embodiment of a system 1 and a device 10 for determining pulse pressure variation of a subject according to the present invention. FIG. 2 shows a flow chart of a corresponding method 100. The system 1 comprises a signal acquisition unit 21 configured to acquire (step S1) an input signal representing a hemodynamic signal of the subject. The signal acquisition unit 21 may e.g. be an arterial line that provides an ABP signal or a photoplethysmographic sensor that provides a PPG signal as input signal. Generally, other options for the signal acquisition unit 21 include elements for acquiring a blood flow signal, a Doppler ultrasound signal, a laser Doppler signal, a speckle-contrast signal, a ballistocardiographic signal, an accelerometer signal, a radio-frequency inductance signal or a bio-impedance signal.

The system 1 further comprises the device 10 for determining pulse pressure variation of a subject based on the acquired input signal (steps S2-S4). The device 10 may e.g. be a processor, a computer or any electronic device, on which software is running for implementing the disclosed method.

The system 1 further comprises a signal issuing unit 22 configured to issue (step S5) the computed pulse pressure variation signal. The signal issuing unit 22 may be a display, e.g. of a computer or user device, for instance a physician's smartphone, or a patient monitor.

The device 10 comprises in an embodiment a processor configured to process the input signal and compute a pulse pressure variation by deriving (step S2) a pulse height (PH) signal from the input signal, deriving (step S3) a pulse height baseline and a de-trended pulse height signal from the pulse height signal, and computing (step S4) the pulse pressure variation from the de-trended pulse height signal and the pulse height baseline. Instead of a processor, the device may comprise respective units or circuitry to carry out these steps, e.g. a first unit 11 for carrying out step S2, a second unit 12 for carrying out step S3 and a third unit 13 for carrying out step S4.

Figure 3:
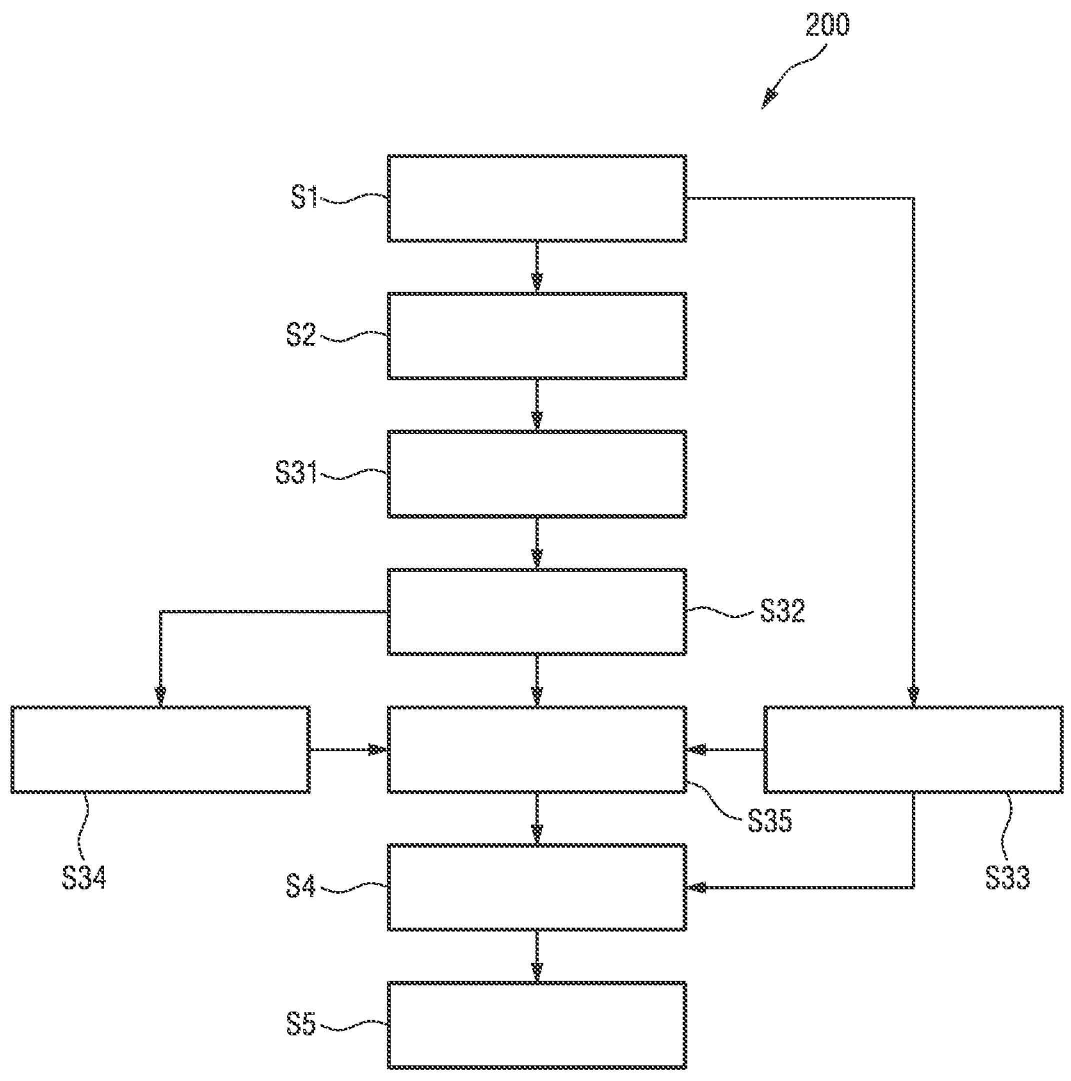
FIG. 3 shows a flow chart of a second embodiment of a method for determining pulse pressure variation of a subject according to the present invention.

FIG. 3 shows a flow chart of a second embodiment of a method 200 for determining pulse pressure variation of a subject according to the present invention. After the extraction of the baseline from the input signal (S1) and the derivation of a continuous PH signal from the pulse height of the input signal (S2), the baseline is extracted from the PH signal (S31). The baseline is then subtracted from the PH signal to obtain a de-trended PH signal (S32). The ventilation frequency can be obtained in various ways: through estimation from the baseline of the input signal (S33) or through estimation from the de-trended PH signal (S34). In another alternative, the ventilation frequency may be obtained as further input from a ventilation frequency sensor, e.g. respiration sensor (such as an accelerometer) arranged at the subject's chest. In still another alternative the ventilation frequency shown in the ventilator may directly be input into the processor automatically or manually.

Subsequently, the de-trended PH signal is optionally filtered using an adaptive band pass filter (e.g. a peak filter) with the ventilation frequency and a desirable bandwidth (S35). Finally, the initial PPV is computed using the baseline and the filtered PH signal (S4), and the obtained PPV is output (S5).

Figure 4:
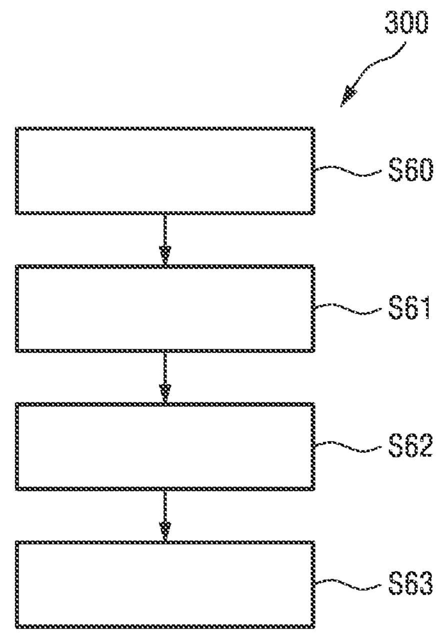
FIG. 4 shows a flow chart of an embodiment of a method for ventilation frequency estimation according to the present invention.

FIG. 4 shows a flow chart of an embodiment of a method 300 for ventilation frequency estimation according to the present invention, which may be used for implementing step S33 or S34. In a first step (S60) the baseline of the input signal or the de-trended PH signal is obtained. In a second step (S61) a Fast Fourier Transform on the obtained signal is performed in a time window of a recent time period (e.g. the recent 30 seconds) that is preferably overlapping with the preceding time window (e.g. by 15 seconds). In a third step (S62) the dominant peak(s) and the ventilation frequency are identified. In a fourth step (S63) the identified ventilation frequency is issued as output.

Figure 5:
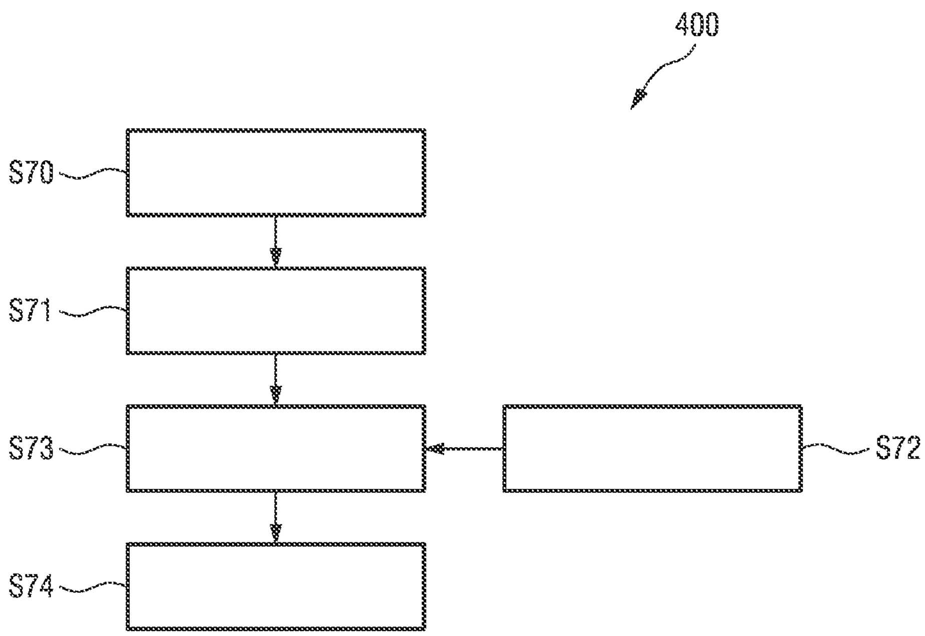
FIG. 5 shows a flow chart of an embodiment of a method for filtering the pulse height signal according to the present invention.

FIG. 5 shows a flow chart of an embodiment of a method 400 for filtering the pulse height signal according to the present invention, which may be used for implementing step S35. In a first step (S70) the updated ventilation frequency and a desired bandwidth are obtained. In a second step (S71) updated filter parameters are obtained or determined. In a third step (S72) the de-trended PH signal is obtained. In a fourth step (S73) the de-trended PH signal is filtered. In a fifth step (S74) the filtered PH signal is issued as output.

Known methods for deriving a PH signal make use of linear interpolation and Gaussian smoothing followed by a low-pass filtering. According to embodiments of the present invention, spline interpolation followed by a low-pass filtering is used to reconstruct missing PH extrema due to the varying phase between cardiac and ventilation cycle.

Next, the post-processing of the PH signal performed before computing the initial PPV. Firstly, the baseline is extracted and separated from the PH signal. In this way, changes in the baseline will not complicate the computation of PPV. In addition, the unwanted components and noise may be filtered out using an adaptive band pass filter. The center frequency of the filter is estimated either from the baseline of the input signal (e.g. an ABP or PPG signal) or from the de-trended PH signal. The bandwidth may be chosen to e.g. 5% of the ventilation frequency. Alternatively, it may also be subject to user configuration (e.g. 0.04 Hz). By using such a filter, the processing focuses on the frequency components close to the ventilation frequency.

Figure 6:
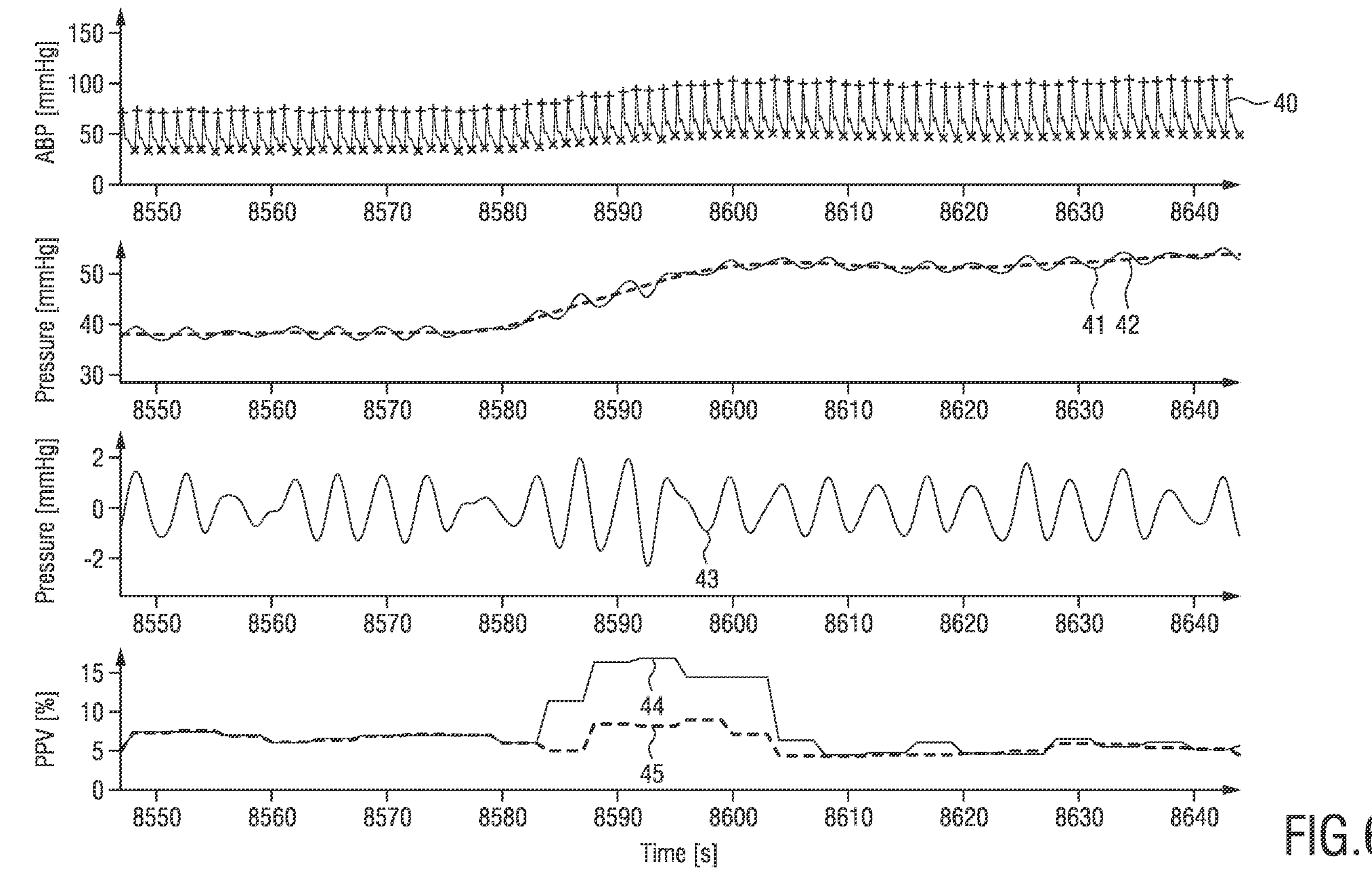
FIG. 6 shows a diagram of various signals used in the method according to the present invention.

The benefit of baseline extraction is illustrated in FIG. 6 showing a diagram of various signals over time used in the method according to the present invention. FIG. 6 shows, as an example of an input signal, an ABP signal 40, a PH signal 41, the baseline 42 of the PH signal 41, a de-trended PH signal 43, a raw PPV signal 44 and a PPV signal 45 after baseline extraction. The change in the baseline 42 manifests itself in the derived maximum and minimum in the PH signal 41. The PPV computed in this situation is not only induced by ventilation, but also the baseline change. After extracting the baseline, the de-trended PH signal 43 is used for computing the difference between the maximum and minimum of the PH and thus the initial PPV signal 44.

Figure 7:
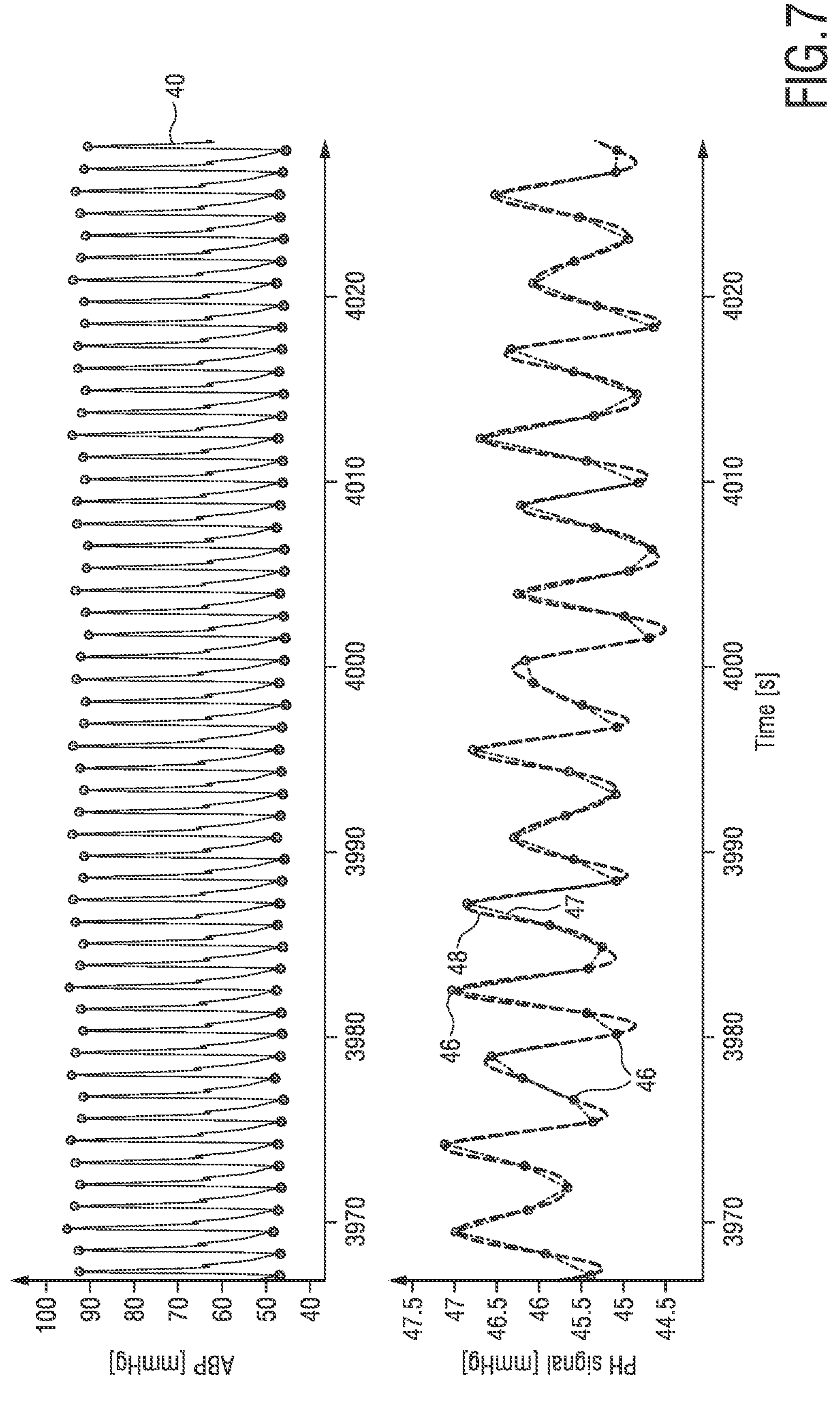
FIG. 7 shows a diagram of various further signals illustrating the effect of the method according to the present invention.
Figure 8:
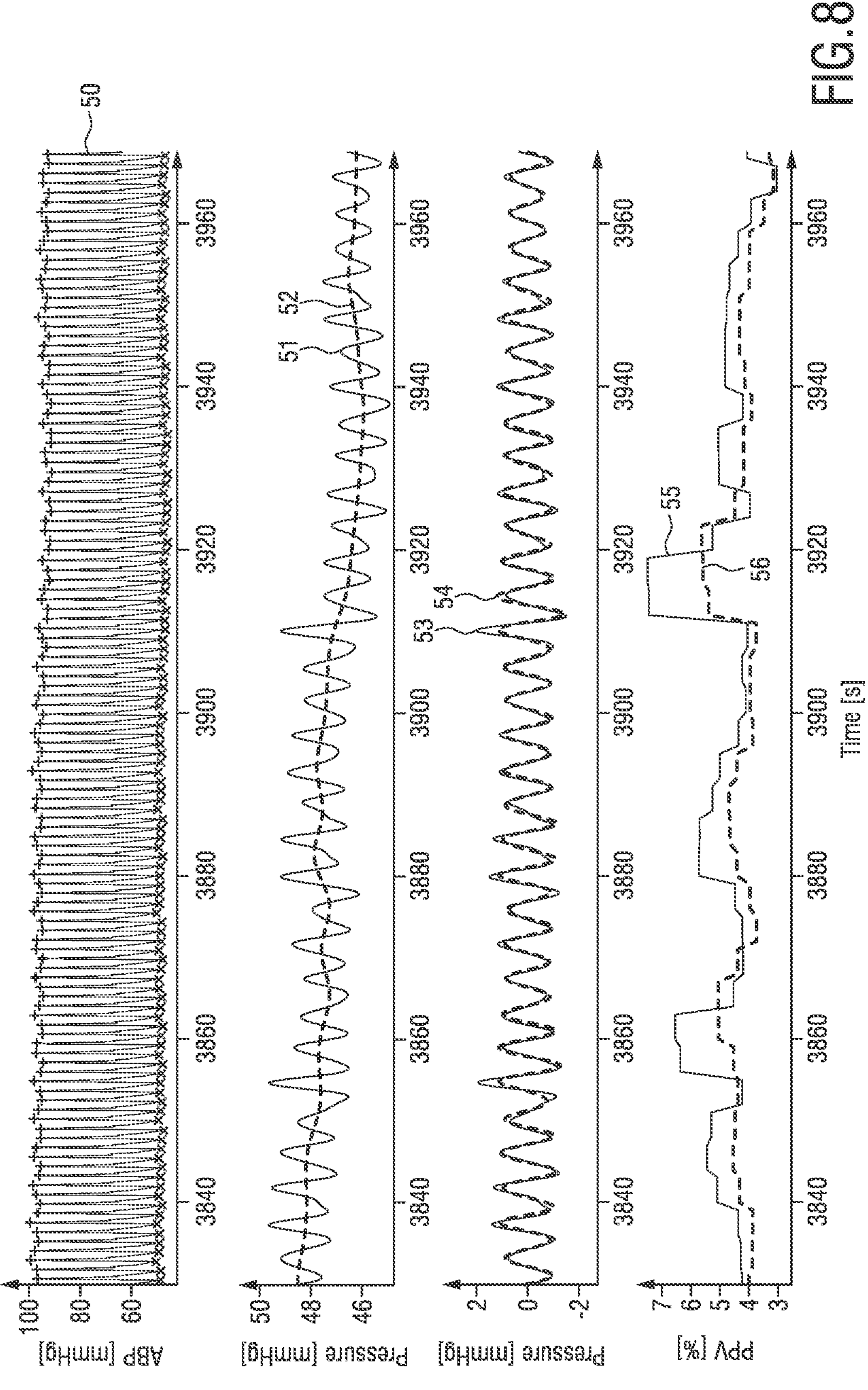
FIG. 8 shows a diagram of various further signals illustrating the effect of adaptive filtering in the method according to the present invention.

The illustration of the influence of varying phase between cardiac and ventilation cycle and the influence of irregular beats are given in FIGS. 7 and 8, respectively. FIG. 7 shows a diagram of various further signals illustrating the effect of the method according to the present invention and FIG. 8 shows a diagram of various further signals illustrating the effect of adaptive filtering in the method according to the present invention. FIG. 7 shows the ABP signal 40, the measured PH values 46, a PH signal 47 obtained from a linear interpolation of the PH values 46 and a PH signal 48 obtained from a spline interpolation of the PH values 46. FIG. 8 shows another ABP signal 50, a resulting PH signal 51, the baseline 52 of the PH signal 51, a de-trended PH signal 53, a filtered de-trended PH signal 54, a raw PPV signal 55 and a PPV signal 56 obtained from the filtered de-trended PH signal 54.

It can be seen from FIG. 7 that the actual maximum and minimum of PH values are approached better by constructing continuous PH signals. In addition, in FIG. 8, filtering the derived PH signal, using an adaptive band pass filter, helps to obtain stable PPV values in the presence of irregular beats by focusing exclusively on the ventilation-induced components.

For computing initial PPV, different sizes of window may be used. It can be chosen between the fixed window length, long enough to cover at least one ventilation cycle, and the estimated ventilation cycle. The fixed window length may be set to a default value, e.g. 8 seconds, and may also be subject to user configuration. The difference between the maximum and minimum of PH is derived from the de-trended PH signal. The average of the maximum and minimum of PH, used for normalization in the formula, is replaced by the baseline of the PH signal.

For post-processing PPV values, three-point mean filter, five-point median filter, suboptimal Kalman filter, and averaging over 15, 30, or longer seconds have been used in known methods. In order to avoid masking real-time changes in the PPV, post-processing PPV values is preferably avoided by the present invention. Nevertheless, the present invention can also be embodied with post processing steps of, for example, a 3, 4 or 5 point median or mean filter.

The present invention may be applied in devices, systems and methods for measurements and monitors. For instance, monitors that compute the PPV value from the blood pressure may make use of the invention to improve the stability and credibility of PPV algorithm. Further, the present invention may be applied in devices, systems and methods for medical consumables and sensors. For instance, disposables for hospitals may make use of the invention, e.g. in capnography systems, photoplethysmography sensors (pulse oximeters) and ventilation masks.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for providing pulse pressure variation of a mechanically ventilated subject, the system comprising:

a signal acquisition unit comprising an arterial line that provides an arterial blood pressure (ABP) signal;

a device comprising:

a signal input configured to receive the ABP signal;

a processor configured to process the ABP signal and compute a pulse pressure variation by:

deriving a pulse height signal from the ABP signal, wherein deriving the pulse height signal comprises spline interpolation and low-pass filtering;

deriving a pulse height baseline from the pulse height signal;

deriving a de-trended pulse height signal by subtracting the pulse height baseline from the pulse height signal;

estimating a ventilation frequency by extracting an ABP baseline and performing a Fast Fourier Transform over a time window of a recent time period with overlap;

filtering the de-trended pulse height signal using an adaptive band-pass filter centered at the ventilation frequency with a bandwidth no greater than 5% of the ventilation frequency; and computing the pulse pressure variation in a computing window equal to an integer number of ventilation cycles from the filtered de-trended pulse height signal and the pulse height baseline as the ratio between the difference between the 95th-percentile and 5th-percentile values of the de-trended pulse height signal within the window and the respective value of the pulse height baseline signal;

a signal output configured to output the computed pulse pressure variation; and a signal issuing unit having a display, the signal issuing unit configured to receive the signal output and provide a representation thereof on the display for consideration by a physician and/or clinician treating the subject.

2. The system of claim 1, wherein the processor is configured to determine the ventilation frequency of the subject from the de-trended pulse height signal.

3. The system of claim 1, wherein the processor is configured to determine the ventilation frequency of the subject by extracting the ventilation frequency from the de-trended pulse height signal.

4. The system of claim 1, wherein the processor is configured to filter the de-trended pulse height signal using a band pass filter around the ventilation frequency of the subject, the band pass filter being a peak filter and having a bandwidth set to five percent of the ventilation frequency or 0.04 Hz.

5. The system of claim 1, wherein the computing window is at least one ventilation cycle.

6. The system of claim 1, wherein the deriving the pulse height signal from the ABP signal comprises spline interpolation.

7. The system of claim 1, wherein the Fast Fourier Transform is performed over a 30-second window with a 15-second overlap.

8. The system of claim 1, wherein the bandwidth of the adaptive band-pass filter is updated whenever the ventilation frequency estimate is updated.

9. The system of claim 1, wherein the signal issuing unit comprises a patient monitor.

10. The system of claim 1, wherein the processor refrains from applying post-processing averaging of the computed pulse pressure variation so as to reduce latency.

* * * * *